(12) United States Patent
Touati

(10) Patent No.: US 11,759,275 B2
(45) Date of Patent: Sep. 19, 2023

(54) ASSEMBLY COMPRISING A SUCTION DEVICE SUITABLE FOR BEING PLACED ON A WOUND AND/OR AN INCISION

(71) Applicant: Gilles Touati, Amiens (FR)

(72) Inventor: Gilles Touati, Amiens (FR)

(*) Notice: Subject to any disclaimer, the term of this patent is extended or adjusted under 35 U.S.C. 154(b) by 488 days.

(21) Appl. No.: 16/629,391

(22) PCT Filed: Jul. 11, 2018

(86) PCT No.: PCT/FR2018/051755
§ 371 (c)(1),
(2) Date: Jan. 8, 2020

(87) PCT Pub. No.: WO2019/012228
PCT Pub. Date: Jan. 17, 2019

(65) Prior Publication Data
US 2021/0128803 A1    May 6, 2021

(30) Foreign Application Priority Data
Jul. 10, 2017 (FR) ...................................... 1756504

(51) Int. Cl.
*A61B 46/00* (2016.01)
*A61M 1/00* (2006.01)
*A61B 46/23* (2016.01)

(52) U.S. Cl.
CPC .............. *A61B 46/00* (2016.02); *A61B 46/40* (2016.02); *A61M 1/84* (2021.05); *A61M 1/915* (2021.05);
(Continued)

(58) Field of Classification Search
CPC .......... A61M 1/90; A61M 1/84; A61B 46/40; A61B 2046/236; A61B 46/00; A61B 2217/005; A61F 13/0203; A61F 13/0216
See application file for complete search history.

(56) References Cited

U.S. PATENT DOCUMENTS 3,763,857 A    10/1973 Schrading
4,089,331 A    5/1978 Hartigan et al.
(Continued)

FOREIGN PATENT DOCUMENTS

WO    2003/018098 A2    3/2003
WO    2009/080922 A1    7/2009

OTHER PUBLICATIONS

International Search Report dated Sep. 25, 2018 in corresponding International application No. PCT/FR2018/051755; 10 pages.

*Primary Examiner* — Sarah Al Hashimi
*Assistant Examiner* — Nhu Q. Tran
(74) *Attorney, Agent, or Firm* — Maier & Maier, PLLC

(57) ABSTRACT

An assembly including a suctioning device suitable for being placed on an incision and/or a wound of a patient to disinfect and/or dry the incision or wound, the device including a drape. The drape includes an outer layer with an upper face and a lower face, the upper face being impermeable, an inner layer, made of non-woven sterile material, including an upper face and a lower face, the lower face to come into contact with the wound and/or the incision. The drape is wound around a limb or around the body of the patient. The assembly also includes a suctioning zone having cavities, a discharge tube connected to the suctioning zone, and a suctioning member is a system for recovering portable or mobile autologous blood.

6 Claims, 4 Drawing Sheets

(52) U.S. Cl.
CPC ........ *A61B 2046/236* (2016.02); *A61M 1/917* (2021.05)

(56) References Cited

U.S. PATENT DOCUMENTS

| | | |
|---|---|---|
| 7,252,089 B1 | 8/2007 | Birnbaum |
| 2005/0028828 A1 | 2/2005 | Heaton et al. |
| 2006/0065275 A1 | 3/2006 | Lamprich et al. |
| 2006/0191540 A1* | 8/2006 | Lamprich ............... A61B 46/23 |
| | | 128/853 |
| 2008/0319362 A1* | 12/2008 | Joseph ..................... A61F 5/01 |
| | | 602/7 |
| 2009/0043268 A1* | 2/2009 | Eddy ..................... A61M 1/734 |
| | | 604/315 |
| 2011/0197897 A1* | 8/2011 | Touati ..................... A61M 1/90 |
| | | 602/42 |
| 2014/0309497 A1 | 10/2014 | Solomon et al. |
| 2015/0209492 A1 | 7/2015 | Blott et al. |
| 2016/0144084 A1* | 5/2016 | Collinson ............... A61L 15/42 |
| | | 604/319 |
| 2016/0361478 A1* | 12/2016 | Eddy ...................... A61P 17/02 |
| 2017/0014275 A1* | 1/2017 | Schneider ............... A61F 13/08 |
| 2017/0202711 A1* | 7/2017 | Cernasov .......... A61F 13/00021 |

\* cited by examiner

ASSEMBLY COMPRISING A SUCTION DEVICE SUITABLE FOR BEING PLACED ON A WOUND AND/OR AN INCISION

FIELD

The invention aims for an assembly comprising a device for suctioning a wound and/or an incision of a patient, as well as the method thereof for installing on said patient, in view of drying and recovering blood loss.

It relates to the technical field of medical accessories making it possible to disinfect and/or dry an incision and/or a wound during a surgical intervention and/or an emergency intervention. It relates more specifically to the technical field of drapes.

BACKGROUND

Numerous current drapes can be used during interventions. For example, during surgical operations, it is common to use drapes equipped with incision windows through which surgical acts are carried out. These areas are placed on the skin of the patient and aim to isolate and to protect the incision area against any contamination. They form an effective barrier between the body of the patient and the atmosphere of the operating room.

These drapes are not totally effective insofar as they do not make it possible to effectively disinfect and/or dry the operating site. Indeed, as soon as the skin is cut, incision secretions appear (bleeding and/or body secretions) which are likely to damage the edges of the incision and cause infections of the wall and/or of the operating site, in particular, hospital-acquired infections. Blood loss observed can be significant and generate an anemia by spoliation. In addition, these secretions mask certain portions of the operating site and therefore impede the correct progress of the surgical intervention. It is therefore necessary to remove the incision secretions, generally by using absorbent compresses that are changed regularly once they are totally soaked. The absorption of secretions by compresses induces additional handling around the operating site, likely to interfere with the practitioner in executing surgical acts. These absorbent compresses are then disposed of and no recovery of this blood volume is possible.

The sterile compress returned to the end of the surgical drape described in patent document U.S. Pat. No. 4,089,331 (KENDALL & CO), does not make it possible to effectively absorb the incision secretions. Indeed, as soon as the compress is totally soaked, the absorption of secretions can no longer be carried out such that it is necessary to continue using additional absorbent compresses and therefore continue to carry out additional handling around the operating site.

In the case of a wound, through patent document WO 2003/018098 (KCI LICENSING INC), a system intended to accelerate the healing of a tissue that is difficult to heal, is known. This system comprises a porous pad introduced in the wound, as well as an airtight dressing attached onto this pad, making it possible for a hermetic closing of the wound. A proximal end of a duct is connected to the dressing, a distal end of this duct could be connected to a depression source, such as an electric pump. A collector installed on the duct makes it possible to retain the exudates suctioned from the wound during the application of a depression. Although effective, this system is complex, and does not protect the wound against possible hospital-acquired infections and has no preventive virtue.

Patent document WO 2009/080922 (TOUATI) proposes to overcome certain abovementioned disadvantages. It describes a suctioning device which is suitable for being placed on an incision and/or a wound of a patient and intended to disinfect an operating site. This device comprises a drape composed of an outer layer comprising an upper face and a lower face, and an inner layer also comprising an upper face and a lower face. The lower face of the inner layer is arranged so as to come into contact with the wound and/or the incision. Although this device constitutes an improvement with respect to the state of the art, the suctioning carried out by this type of device is extremely limited and does not make it possible, in any case, to auto-transfuse the blood of the patient during the intervention.

Patent document US 2005/0028828 (HEATON) discloses a suctioning device suitable for being placed on an incision and/or a wound of a patient. This device comprises a sterile drape comprising an outer layer provided with a suctioning head and an inner layer suitable for coming into contact with the wound and/or the incision. The inner layer and the outer layer are two separate parts. The practitioner must first implement the inner layer on the wound and/or the incision, then must cover it with the outer layer which is returned. Different steps are also necessary for the implementation of the suctioning device, which can be not only tedious, but also expensive over time, and therefore in practice, not very suitable for emergencies.

SUMMARY

The invention aims to overcome this state of affairs. In particular, an aim of the invention is to propose a device capable of disinfecting the edges of the wound and/or the incision more effectively than the solutions proposed in the prior art.

Another aim is to propose a device which could be used in emergencies and making it possible to reuse blood lost by the patient, during a traumatic wound.

Also, another aim, is to propose a device which is easy and comfortable to use by the practitioner.

The solution proposed by the invention is an assembly comprising:
  a suctioning device suitable for being placed on an incision and/or a wound of a patient to disinfect and/or dry said incision or said wound, said device comprising a drape composed of:
    an outer layer comprising an upper face and a lower face,
    an inner layer comprising an upper face and a lower face, which lower face is arranged so as to come into contact with the wound and/or the incision.
  a suctioning member.
This assembly is noteworthy, in that:
  the upper face of the outer layer of the drape is impermeable,
  the drape is suitable for being wound around a limb or around the body of the patient,
  the outer layer and the inner layer of the drape are made of one single part, such that the winding of said drape around a limb or around the body of the patient leads to the simultaneous winding of said outer layer and of said inner layer,
  a suctioning zone having cavities, is arranged between the lower face of the outer layer and the upper face of the inner layer, the periphery of said suctioning zone being sealed, a discharge tube is connected to the suctioning zone, said tube ending with a nozzle suitable for being connected to the suctioning member to create a suctioning depression in the suctioning zone, the suctioning member is a system for recovering portable or mobile autologous blood.

Thanks to this device, the drape can be wound quickly around a limb or around the body of a patient if hemorrhages are massive. Through the design thereof, the suctioning zone and the cavities thereof make it possible to quickly collect a large volume of blood which will be able to be recycled and reused, in particular in the case of an auto-transfusion. The wound and/or the incision furthermore remains relatively clean and/or dried, such that the general state of a patient or an injured person can be stabilized.

Other advantageous features of the invention are listed below. Each of these features can be considered individually or combined with the noteworthy features defined above, and form the subject, if necessary, of one or more divisional patent applications:

the inner layer can be constituted of a neutral gauze, so as to minimize the interactions with red blood cells, the suctioning zone can be composed of a multiperforated catheter maze, the suctioning zone can be composed of multiperforated foam, the suctioning zone can be composed of a catheter grid network, the drape can be composed of a separable male portion and a female portion, a total or partial incision window can be installed in the drape, so as to have access to the wound and/or the incision.

The invention also relates to a method for installing an assembly according to the invention comprising steps consisting of:

positioning the suctioning protective device by:

placing the lower face of the inner layer of the drape, facing the incision and/or facing the wound, winding the drape around the limb or around the body of the patient where the incision and/or the wound is situated, connecting the suctioning member to the nozzle of the discharge tube.

BRIEF DESCRIPTION OF THE FIGURES

Other advantages and features of the invention will best appear upon reading the description of a preferred embodiment below, in reference to the appended drawings, made as indicative and non-limiting examples, and wherein.

DETAILED DESCRIPTION

The invention relates to an assembly comprising a device for suctioning a wound and/or an incision intended to disinfect them and/or dry them for autologous blood recovery and possibly to avoid the development of infections. Such a suctioning device comprises a drape 1 constituted of two layers 3, 4 surrounding a suctioning zone 6a, 6b, 6c.

Figure 1:
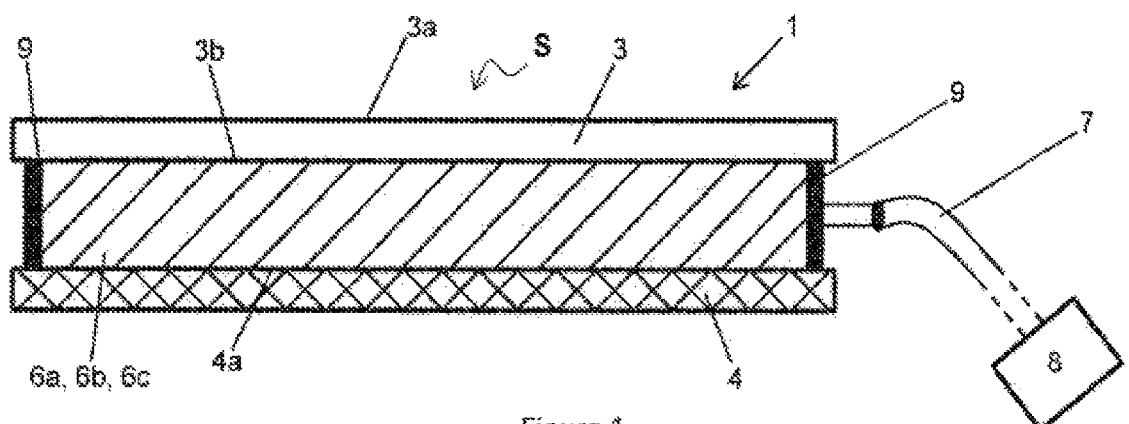
FIG. 1 is a schematic, cross-sectional view of a drape constituting a suctioning device according to the invention.

In FIG. 1, the drape comprises a suctioning zone 6a, 6b, 6c arranged between an outer layer 3 and an inner layer 4.

The outer layer 3 comprises an upper face 3a and a lower face 3b in contact with the suctioning zone 6a, 6b, 6c (described above in the description). This layer 3 can, for example, be made of a non-woven sterile material of the cellulose cotton type, single-layer or multilayer. Any other material known to a person skilled in the art and suiting the production of the drape 1 can however be used.

Preferably, and with the aim of effectively isolating the body of the patient P of the outer environment and in particular, introducing a contaminated fluid, the upper face 3a of the outer layer 3 of the drape 1 is preferably impermeabilized. This impermeabilization can be done by means of a plastic film, of a material which is impermeable to liquids, of a hydrophobic material, or also using any other material suiting a person skilled in the art.

The inner layer 4 comes into contact with the patient P when the suctioning device is installed. It makes it possible to avoid the suctioning zone 6a, 6b, 6c (described above in the description) being in direct contact with the incision and/or the wound, and thus improves the comfort and the safety of the patient P. Preferably, the inner layer 4 is presented in the form of a neutral gauze such that it is the least amount of interactions possible with the red blood cells contained in the blood of the patient P. Thus, the embodiment preferred for the inner layer 4 is a neutral gauze of a known type, like for example, sterile compresses.

In the same manner as the outer layer 3, the inner layer 4 can be made of a non-woven sterile material of the cellulose cotton type, single-layer or multilayer. Any other material known to a person skilled in the art and suiting the production of a drape 1 can however be used.

The outer layer 3, as well as the inner layer 4 each have a width of between 20 cm and 40 cm, a total length of between 20 cm and 60 cm, and a thickness varying from 1 mm to 2 mm. However, these dimensions are not limiting and can be adapted by the person skilled in the art, according to the type of surgical intervention carried out.

In a preferred embodiment, the inner layer 4 and the outer layer 3 are made of one single part surrounding the suctioning zone 6a, 6b, 6c. Such a configuration makes it possible to facilitate the design of the suctioning protective device and thus limit the costs.

The suctioning zone 6a, 6b, 6c is arranged between the upper face 4a of the inner layer 4 and the lower face 3b of the outer layer 3. It comprises cavities 61a, 61b, 61c, wherein the blood of the patient P will be collected then suctioned, in order to be able to recycle it and thus reuse it.

The suctioning zone 6a, 6b, 6c is connected to a suctioning member 8 by means of a tube 7. The tube 7 is advantageously perforated on a distal portion, and ends, on the proximal portion thereof, by a nozzle intended to be connected to the suctioning member 8. In practice, a Luerlock® connector is used, which could be connected to a pump or any other type of suctioning member.

The suctioning member 8 is preferably presented in the form of a system for recovering autologous blood of Cell Saver® type. Such a device makes it possible for the practitioner, after washing and centrifugation, to auto-transfuse the patient P during the intervention. Such a feature being particularly useful during emergency intervention or also to avoid risks of allogenic transfusions. This recovery system 8 is preferably portable, so as to be able to transport it easily over the places of intervention. It can, however, in the case of an intervention occurring in an operating room, being presented in the form of a wall-fixed system. It can create a suctioning depression which could vary between −50 mmHg and −300 mmHg, thus making it possible for the practitioner to adjust the suctioning force according to the degree of hemorrhage.

The suctioning zone 6a, 6b, 6c is sealed, the periphery 9 thereof being closed such that the suctioned blood in said suctioning zone 6a, 6b, 6c can only escape through the tube 7. The sealing can be achieved through welding, or also by adding a material surrounding the whole periphery 9. The suctioning zone 6a, 6b, 6c has dimensions similar to those of the inner 4 and outer 3 layers. It has a length of between 20 cm and 60 cm, a width varying from 20 cm to 40 cm, and a thickness of between 1 mm and 1 cm.

In a first embodiment, the suctioning zone 6a is presented in the form of a multiperforated catheter maze 63a. The catheters of this multiperforated catheter maze 63a are known to a person skilled in the art and can be made of materials such as polyimide or also polyurethane. The number of catheter in the multiperforated catheters maze 63a can vary according to the necessary suctioning capacity. The suctioning zone 6a can, for example, comprise between 1 and 100 catheters.

Figure 6:
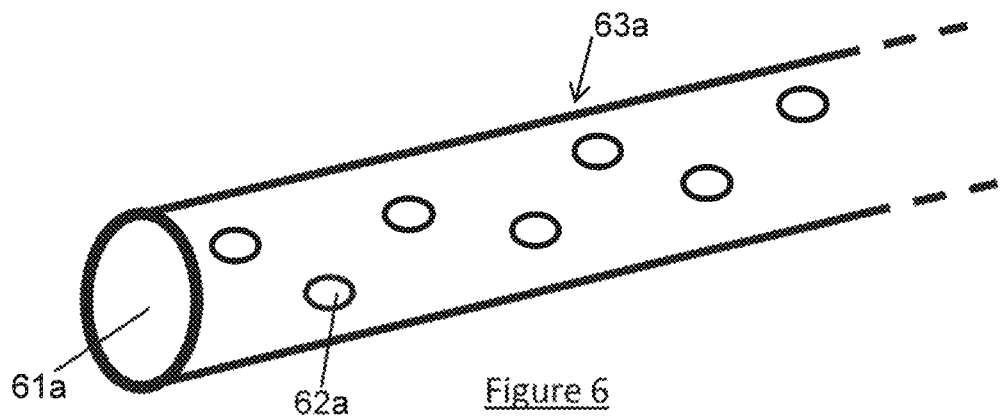
FIG. 6 is a schematic view of a multiperforated catheter used in the suctioning zone of a drape used in the invention.

FIG. 6 illustrates a catheter of such a multiperforated catheter maze 63a. In this embodiment, the ducts of each of the catheters of the multiperforated catheter maze 63a constitute the cavities 61a wherein the blood of the patient P will be suctioned. The suctioning depression created by the system 8 will suction the blood through perforations 62a so as to recover it in the ducts 61a and then transfer it to said recovery system 8.

Figure 7:
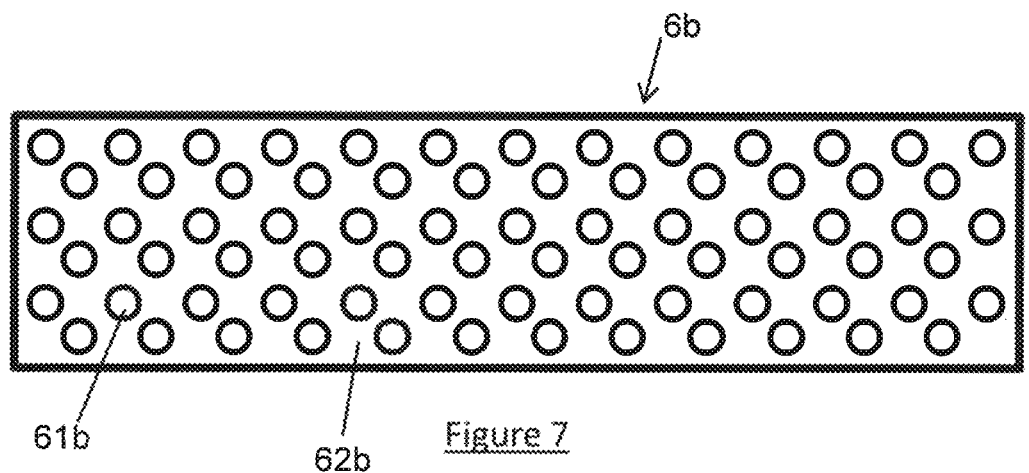
FIG. 7 is a schematic view of a suctioning zone example, this being presented in the form of a multiperforated foam.

A second embodiment represented in FIG. 7, has a suctioning zone 6b being presented in the form of a multi-perforated foam. This foam comprises cavities 61b, preferable arranged uniformly in the whole of the foam 6b. In the same manner as in the preceding embodiment, the suctioning depression created by the system 8 will suction the blood into the cavities 61b through the foam 62b to then send it to said blood recovery system 8.

Figure 8:
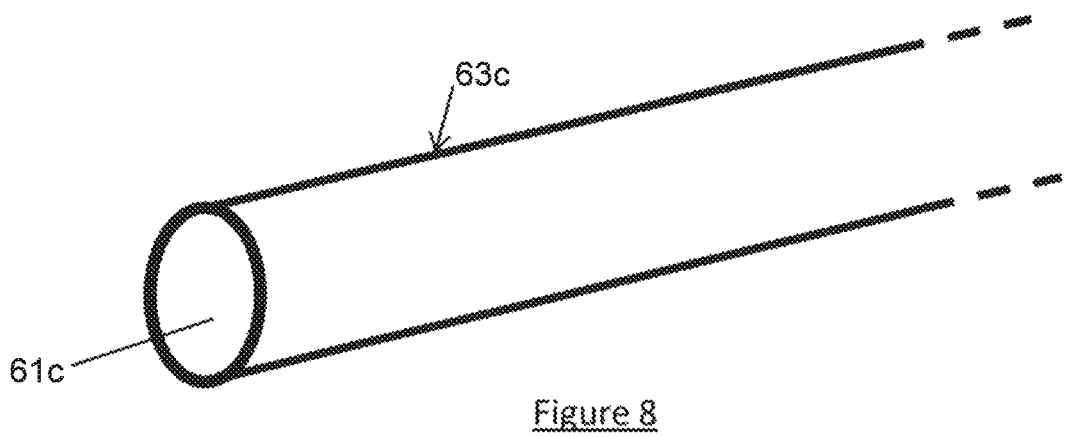
FIG. 8 is a schematic view of a catheter of a known type, used in an embodiment of the suctioning zone according to the invention.

In an alternative embodiment, the suctioning zone 6c can be composed of a catheter grid network 63c (represented in FIG. 8). The grids can be interconnected with one another or be separated. In the last case, each of the grids will be connected independently to the recovery system 8. Similarly to that described in the first embodiment, the ducts of the catheters 63c constitute the cavities 61c wherein the suctioned blood is housed. When the suctioning depression is applied using the system 8, the blood of the patient P is suctioned then retransferred to said system so as to be treated and then re-transfused.

Figure 2:
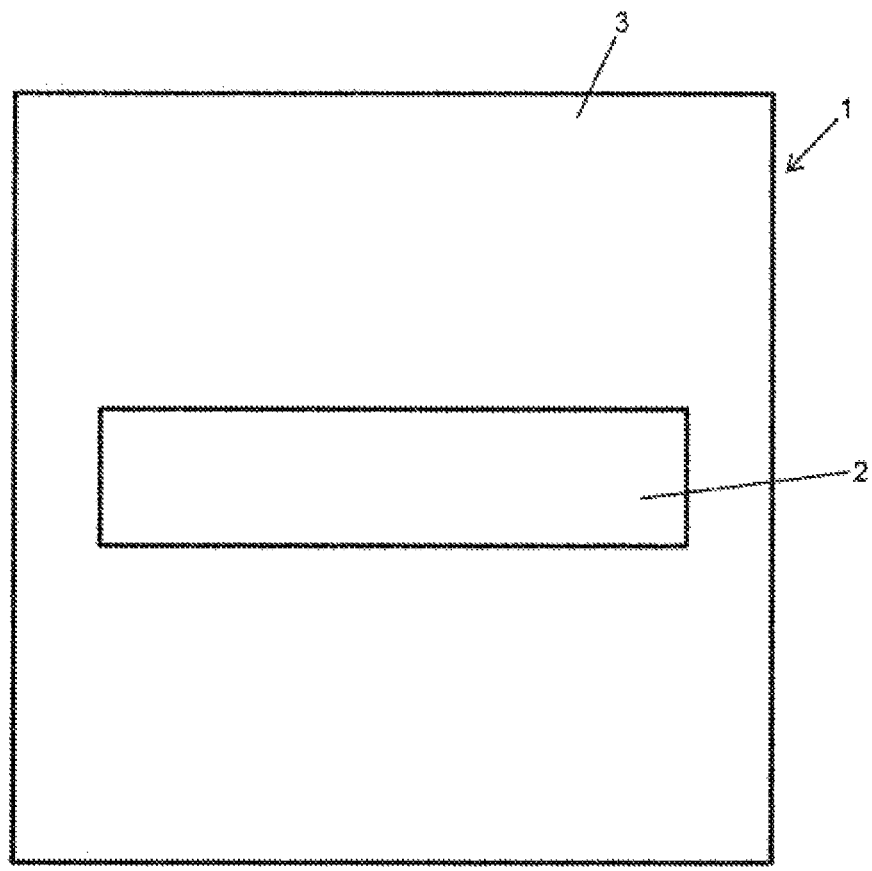
FIG. 2 is a schematic, top view of the drape of FIG. 1, this being equipped with an incision window.

FIG. 2 illustrates a preferred embodiment of the invention, wherein the suctioning device comprises an incision window 2. This can be partial or total and makes it possible for the practitioner to carry out an intervention. This embodiment is particularly useful when the device is used during a surgical intervention and that it is placed at the level of an incision.

In FIG. 2, the drape 1 is made of one single part. It can however be formed of a separable male portion 1a and a female portion 1b (FIG. 3), the incision window 2 being arranged at the level of the junction between said male portion 1a and said female portion 1b. The use of a drape 1 made of two separable portions 1a, 1b simplifies the design thereof and the implementation thereof by the practitioner. In addition, such a drape 1 makes it possible to make the size of the incision window 2 vary and thus make it possible for the practitioner to adjust it according to the operation to be carried out. To adapt the size of the incision window 2 to the size of the incision or of the wound, the male portion 1a and the female portion 1b of the drape 1 are maintained in position by an adjustable attachment device making it possible to adjust the position of said male portion 1a with respect to said female portion 1b and to make the size of said incision window 2 vary.

Figure 3:
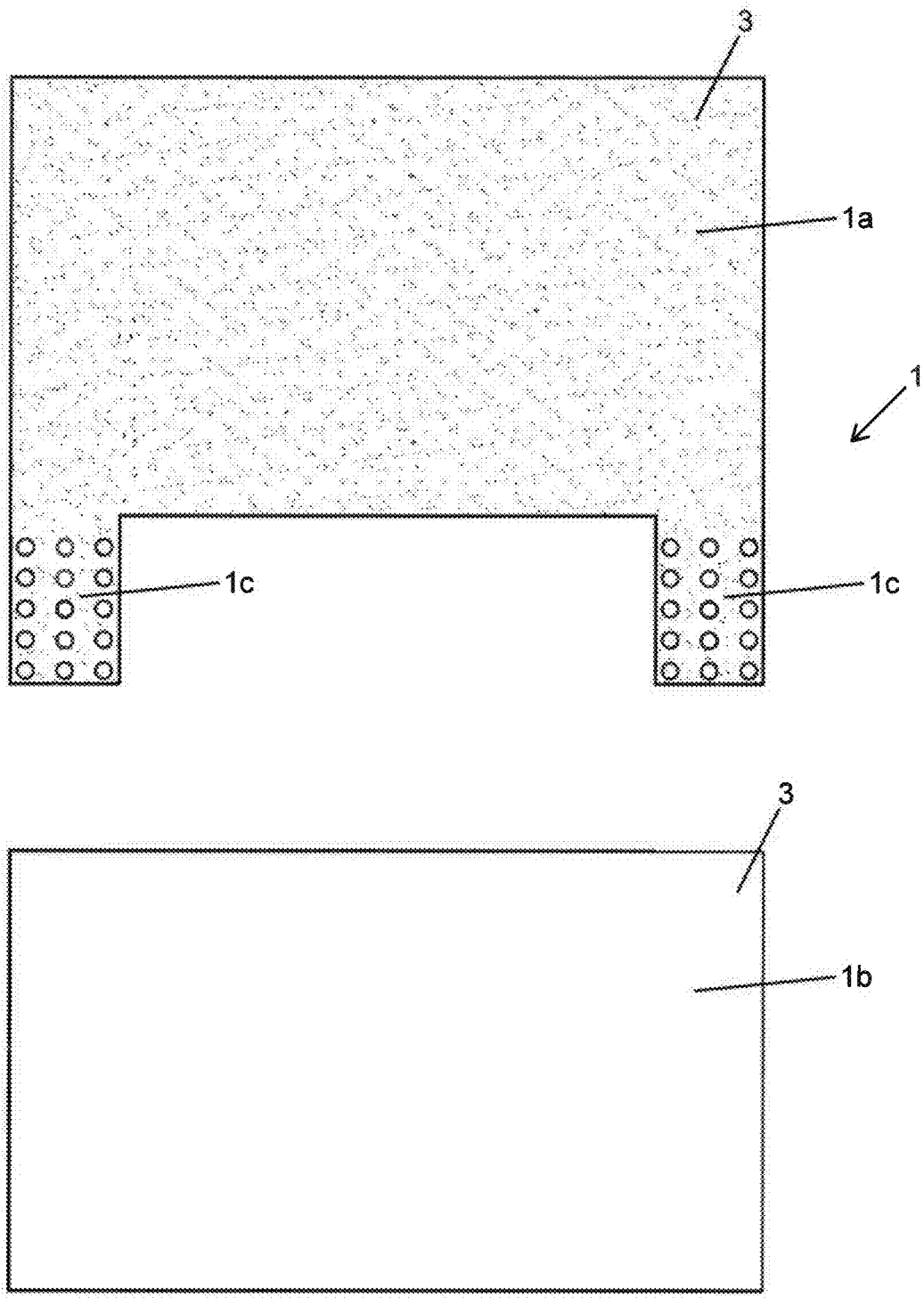
FIG. 3 is a schematic, top view of a drape according to the invention, said drape being constituted of a separable female portion and male portion.

By referring to FIG. 3, the adjustable attachment device is preferably formed of adhesive attachment pads 1c arranged on the male portion 1a and capable of adhering onto the female portion 1b. The adhesive zones can possibly be protected by a removable protective paper that the operator will remove just before the implementation. Any other equivalent adjustable attachment device can be used by a person skilled in the art, like for example, loop straps and hook straps of the VELCRO® type, or also male elements being inserted into female elements.

Figure 4:
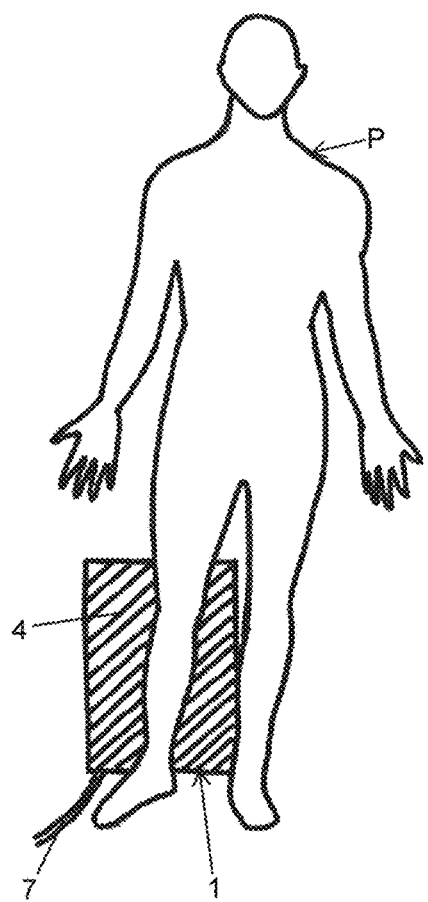
FIG. 4 is a schematic view of a patient, the suctioning device of FIG. 1 being installed under the limb of said patient.
Figure 5:
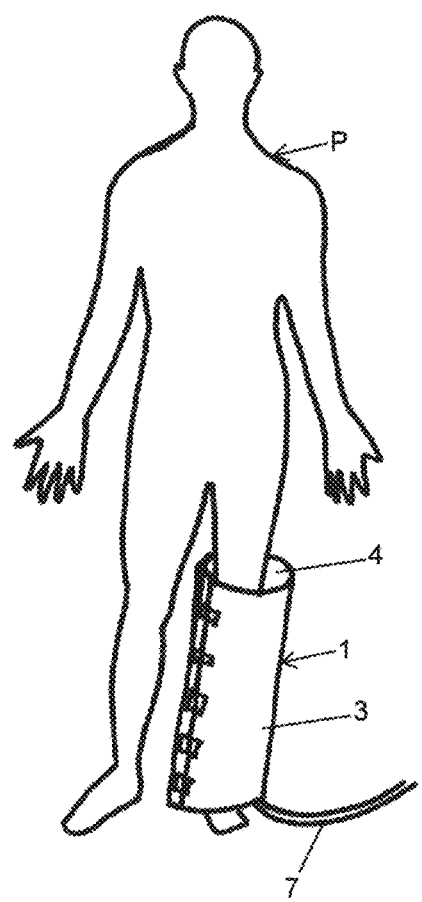
FIG. 5 is a schematic view of a patient, the suctioning device of FIG. 1 being wound around the limb of said patient.

FIGS. 4 and 5 represent examples of installing the suctioning device. The limb of the patient P can be placed on the drape 1 (FIG. 4). This configuration is particularly practical when a practitioner operates in an emergency and/or when the blood loss flow is increased.

In another embodiment represented in FIG. 5, the drape 1 is wound around the limb or the body of the patient where the wound and/or the incision is situated, thus making it possible to maximize the recovery of the blood during an intervention. In this embodiment, the drape 1 preferably has an attachment device 5 making it possible to maintain it in position after having positioned it. This device can, for example, be presented in the form of Velcro® straps, or also a device of the pressure-button type.

The winding of the drape 1 leads to the simultaneous winding of the outer layer 3 thereof and of the inner layer 4 thereof. The suctioning device can therefore be implemented easily and quickly, in extreme emergency situations, in one single step, contrary to the device described in patent document US2005/0028828 (HEATON), of which the implementation requires several steps.

The arrangement of the different elements and/or means and/or steps of the invention, in the embodiments described above, must not be understood as requiring such an arrangement in all the implementations. In any case, it will be understood that various modifications can be applied to these elements and/or means and/or steps, without moving away from the sense and the scope of the invention. In particular:

the drape 1 can be positioned differently than the placements described above. It can, for example, be placed at the level of one of the arms, of the torso, etc., the suctioning zone 6a, 6b, 6c can be different from that described. It can, for example, be presented in the form of a combination of embodiments detailed above.

the suctioning zone 6a, 6b, 6c can be equipped of several tubes 7, making it possible to connect it simultaneously to several suctioning members 8, the shape of the drape 1 can be different from that described above. It can vary according to the position of the incision and/or the wound. It can, for example, be presented in the shape of a circle, of an ellipsis, or also any other shape suiting a person skilled in the art.

The invention claimed is:

1. An assembly for suctioning and collecting blood flowing from an incision and/or a wound on a limb or on the body of a patient, comprising:
  a suctioning device for suctioning the blood,
  wherein the suctioning device comprises a drape configured for placement on an incision or on a wound located on a limb or on the body of a patient and for winding around said limb or said body in order to collect the blood produced by said incision or said wound, the drape comprising:
    an outer layer comprising an upper face and a lower face;
    an inner layer comprising an upper face and a lower face, wherein the lower face of said inner layer is arranged so as to come into contact with said wound or said incision, and is made of neutral gauze, so as to minimize the interactions with red blood cells of the blood, and
  a suctioning organ configured to suck and recycle the blood collected in the drape, and a discharge tube connecting said suctioning organ to said suctioning device;
  wherein the upper face of the outer layer of the drape is impermeable,
  wherein the lower face of the inner layer is made of neutral gauze, so as to minimize the interactions with red blood cells of the blood,
    the lower face of said outer layer and the upper face of said inner layer are separated by a suctioning zone having cavities and being sealed at its periphery, said suctioning zone being connected to the end of said discharge tube which is connected to said suctioning device;
    wherein the outer layer and the inner layer of said drape are made of one single part such that the winding of said drape around said limb of said body of the patient leads to the simultaneous winding of said outer layer and said inner layer, and also of said suctioning zone,
    wherein the suctioning organ is an autologous blood recovery system.

2. The assembly according to claim 1, wherein the suctioning zone is formed of a multiperforated catheter maze.

3. The assembly according to claim 1, wherein the suctioning zone is formed of multiperforated foam.

4. The assembly according to claim 1, wherein the suctioning zone is formed of a catheter grid network.

5. The assembly according to claim 1, wherein the drape is formed of a separable male portion and a female portion.

6. A method for installing an assembly for suctioning and collecting blood flowing from an at least one of an incision and/or a wound on a limb or on the body of a patient, comprising:
  a suctioning device comprising a drape configured for placement on an incision or on a wound located on a limb or on the body of a patient and for winding around said limb or said body in order to collect blood produced by said incision or said wound, said drape comprising:
    an outer layer comprising an upper face and a lower face,
    an inner layer comprising an upper face and a lower face, wherein the lower face of said inner layer is arranged so as to come into contact with said wound or said incision, and is made of neutral gauze, so as to minimize the interactions with red blood cells of the blood,
  wherein the upper face of the outer layer of the drape is impermeable, and
  a suctioning organ adapted to suck and recycle the blood collected by the drape, and a discharge tube connecting said suctioning organ to said suctioning device, and
  the lower face of said outer layer and the upper face of said inner layer are separated by a suctioning zone having cavities and being sealed at its periphery, said suctioning zone being connected to the end of said discharge tube, which is connected to said suctioning device;
  wherein the outer layer and the inner layer of the drape are made of one single part such that the winding of said drape around a limb of the body of the patient leads to the simultaneous winding of said outer layer and said inner layer,
  and
  wherein the suctioning organ is an autologous blood recovery system,
  wherein the method comprises the steps of:
    placing said drape over said wound or said incision in such a manner that the lower face of said inner layer comes into contact with said wound or said incision and winding said drape around said limb or around said body in order to collect the blood produced by said wound or by said incision,
    and
    sucking and recycling the blood collected in said drape by using said autologous blood recovery system.

* * * * *